United States Patent [19]

Stach, deceased et al.

[11] 4,238,506
[45] Dec. 9, 1980

[54] HYPOGLYCAEMICALLY AND HYPOLIPIDAEMICALLY ACTIVE DERIVATIVES OF PHENYL-ALKANE-CARBOXYLIC ACIDS

[75] Inventors: Kurt Stach, deceased, late of Mannheim-Waldhof, Fed. Rep. of Germany, by Werner Plattner, executor; Elmar Bosies, Heppenheim, Fed. Rep. of Germany; Ruth Heerdt, Mannheim-Feudenheim, Fed. Rep. of Germany; Hans-Frieder Kühnle, Mannheim-Neuostheim, Fed. Rep. of Germany; Felix H. Schmidt, Mannheim-Seckenheim, Fed. Rep. of Germany

[73] Assignee: Boehringer Mannheim GmbH, Mannheim, Fed. Rep. of Germany

[21] Appl. No.: 920,508

[22] Filed: Jun. 29, 1978

Related U.S. Application Data

[62] Division of Ser. No. 674,993, Apr. 8, 1976, Pat. No. 4,113,871.

[30] Foreign Application Priority Data

Apr. 18, 1975 [DE] Fed. Rep. of Germany ....... 2527229

[51] Int. Cl.$^3$ .......................................... C07C 101/42
[52] U.S. Cl. .................................. 424/319; 562/442; 424/258; 424/275; 546/169; 549/71
[58] Field of Search ............... 424/319, 309, 258, 275; 560/37, 42; 562/442, 451; 260/332.2 C; 546/169

[56] References Cited

U.S. PATENT DOCUMENTS

| | | | |
|---|---|---|---|
| 3,781,328 | 12/1973 | Witte et al. | 562/451 |
| 4,010,279 | 3/1977 | Griss et al. | 562/451 |
| 4,026,896 | 5/1977 | Harita et al. | 424/319 |

FOREIGN PATENT DOCUMENTS 2500157  7/1976  Fed. Rep. of Germany ........... 562/451

*Primary Examiner*—James H. Reamer

[57] ABSTRACT

Phenyl-alkane-carboxylic acids of the formula

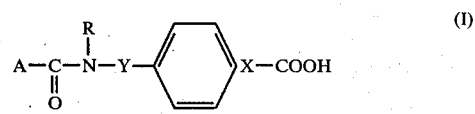

wherein
A is an aryl, aralkyl or arylvinyl radical optionally substituted by hydroxy, halogen, trifluoromethyl, alkyl, alkylthio, alkoxy, alkenyloxy, alkoxyalkoxy, alkyl-substituted amino, aryloxy or alkoxy-substituted aryloxy, or is an aryloxyalkyl or arylthioalkyl radical, or a heterocyclic ring system optionally substituted by halogen, alkyl or alkoxy,
Y is a valency bond or an unbranched or branched lower alkylene radical containing up to 3 carbon atoms,
X is a straight or branched, saturated or unsaturated divalent aliphatic hydrocarbon radical containing 2 to 8 carbon atoms, there being at least 2 carbon atoms between the benzene ring and the carboxyl group, and
R is a hydrogen atom or a lower alkyl radical, as well as physiologically compatible salts, esters and amides thereof, exhibit hypoglycaemic and hypolipidaemic activity.

9 Claims, No Drawings

HYPOGLYCAEMICALLY AND HYPOLIPIDAEMICALLY ACTIVE DERIVATIVES OF PHENYL-ALKANE-CARBOXYLIC ACIDS

This is a division of application Ser. No. 674,993 filed Apr. 8, 1976, now U.S. Pat. No. 4,113,871.

The percent invention is concerned with new phenyl-alkane-carboxylic acid derivatives and with the preparation thereof.

The new phenyl-alkane-carboxylic acid derivatives according to the present invention are compounds of the general formula:

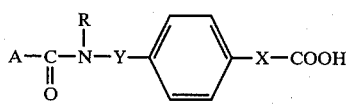

wherein A is an aryl, aralkyl or arylvinyl radical optionally substituted by hydroxy, halogen, trifluoromethyl, alkyl, alkylthio, alkoxy, alkenyloxy, alkoxyalkoxy, alkyl-substituted amino, aryloxy or alkoxy-substituted aryloxy, or is an aryloxyalkyl or arylthioalkyl radical or a heterocyclic ring system optionally substituted by halogen, alkyl or alkoxy, Y is a valency bond or an unbranched or branched lower alkylene radical containing up to 3 carbon atoms, X is a straight or branched, saturated or unsaturated divalent aliphatic hydrocarbon radical containing 2 to 8 carbon atoms, there being at least 2 carbon atoms between the benzene ring and the carboxyl group, and R is a hydrogen atom or a lower alkyl radical; and the physiologically compatible salts, esters and amides thereof.

The new compounds according to the present invention have hypoglycaemic and/or hypolipidaomic properties.

The alkyl and alkoxy radicals are to be understood to be, in all cases, straight or branched radicals containing up to 5 carbon atoms. The preferred straight chained alkyl radical is the methyl radical, the preferred branched alkyl radical is the tert.-butyl radical and the preferred alkylthio radical is the methylthio radical. Alkyl-substituted amino is preferably dimethylamino. The alkonyloxy radical is to be understood to be one containing up to 5 carbon atoms and is preferably an allyloxy radical. The aryloxy radical in preferably a phenoxy radical and the alkoxyalkyoxy radical is preferably one containing 2 to 5 carbon atoms, especially a methoxyethoxy radical. The aryl radical is to be understood to be an aromatic radical containing 6 to 10 carbon atoms, especially a naphthyl or phenyl radical.

Aralkyl is preferably an α-phenylethyl radical, or a β-phenylethyl radical substituted by tert.-butyl and/or hydroxyl, as well as a fluorenyl-(9)-methyl radical and arylvinyl is preferably a styryl radical optionally substituted by halogen and/or alkoxy. The aryloxyalkyl and arylthioalkyl radicals are preferably phenoxymethyl or phenylthiomethyl radicals.

The optionally substituted heterocyclic ring system in preferably a thienyl, pyrazolyl, isoxazolyl, pyridyl, pyrazinyl, chromanyl, quinolyl, indolyl, benzoxazolyl or optionally partially hydrogenated benzofuranyl radical.

By halogen, there is to be understood fluorino, chlorine or bromine.

As mentioned above, the new compounds of general formula (I) and their physiologically compatible salts, esters and amides have surprisingly outstanding hypoglycaemic and/or hypolipidaemic properties.

The new compounds of general formula (I) can be prepared, for example, by one of the following processes:

(a) reaction of an amine of the general formula:

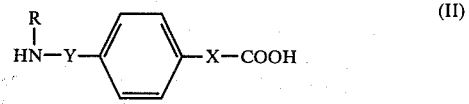

wherein Y, X and R have the same meanings as above, or an acid derivative thereof with a reactive derivative of an acid of the general formula A.COOH, wherein A has the same meaning as above; or (b) oxidation of a compound of the general formula:

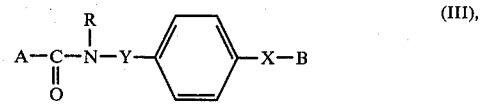

wherein A, Y, R and X have the same meanings as above and B is a group convertible into a carboxyl group; or (c) reduction of a compound of the general formula:

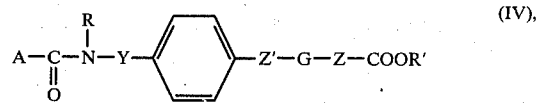

wherin A, R and Y have the same meanings as above, Z is a straight chain or branched, saturated or unsaturated divalent aliphatic hydrocarbon radical containing up to 7 carbon atoms, Z' has the same meaning as Z or is a valency bond, R' is a hydrogen atom or an alkyl radical and G is the group —CO— or —CH(L)—, wherein L is a halogen atom or a hydroxyl group; or (d) reaction of a compound of the general formula:

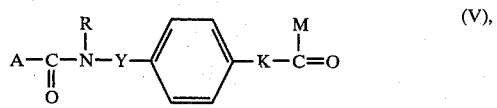

wherein A, R and Y have the same meanings as above, M is a hydrogen atom or an alkyl radical containing up to 6 carbon atoms and K is a valency bond or a straight or branched chain, saturated or unsaturated divalent aliphatic hydrocarbon radical containing up to 6 carbon atoms, with a reactive methylene component of the general formula:

wherein P is a hydrogen or alkali metal atom or a lower alkyl or acyl radical and Q is a hydrogen atom or a nitrile group or an alkyl radical containing up to 6 carbon atoms or the radical —COOP—, wherein P has the same meaning as above; whereafter, if necessary, the compound obtained is subsequently saponified, decarboxylated or hydrogenated; or (e) for the case in which X in general formula (I) is a straight or branched saturated divalent aliphatic hydrocarbon radical containing 2 1 to 4 carbon atoms, reaction of a compound of the general formula:

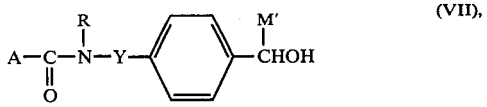

wherein A, R and Y have the same meanings as above and M' is a hydrogen atom or methyl or ethyl radical, with a compound of the general formula:

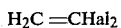 (VIII), wherein Hal is a halogen atom; or (f) for the case in which X in general formula (I) is a straight-chained, saturated divalent aliphatic hydrocarbon radical containing 2 to 4 carbon atoms, reaction of a ketone of the general formula:

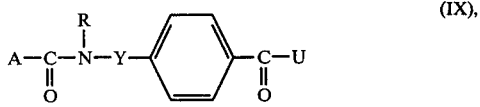

wherein A, R and Y have the same meanings as above and U is an alkyl radical containing 2 to 4 carbon atoms, under the conditions of the Hillgerodt-Kindler synthesis; or (g) reaction of a halogen compound of the general formula:

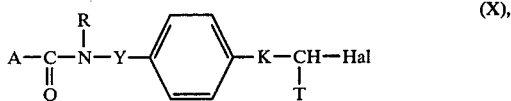

wherein A, R, Y, K and Hal have the same meanings as above and T is a hydrogen tom or an alkyl radical containing up to 6 carbon atoms, with a reactive methylene component of the general formula:

wherein R$_2$ is a lower alkyl radical, R$_1$ is a hydrogen atom or an alkyl radical containing up to 6 carbon atoms, Me is an alkali metal or alkaline earth metal atom and W is the radical OR$_2$ or a methyl radical, followed by saponification and, if necessary, decarboxylation; whereafter acid derivatives obtained of general formula (I) are, if desired, converted into the free acids or the free acids obtained of general formula (I) are, if desired, esterified or converted into physiologically compatible amides or acid-addition salts.

In the case or process (a), the reactive derivative of the acid A.COOH is preferably the acid chloride, which can be obtained in known manner by the reaction of the carboxylic acid with thionyl chloride. However, the esters, azides, anhydrides or mixed anhydrides can also be employed equally well. The reaction with the compound of general formula (II) can be carried out by the Schotten-Baumann method. If it is desired to operate under anhydrous conditions, then it is preferable to use anhydrous pyridine or methylene chloride with the addition of a tertiary amino, for example triethylamine. Instead of the free amino compound, a salt thereof can also be used.

As acid derivatives of the compounds of general formula (II), there can be used, for example, the esters, especially the methyl and ethyl esters, nitriles, acid amides or acid anhydrides, whch can then, if necessary, be converted in known manner into the desired carboxyl, ester or amide group.

The compounds of general formula (II) are new and can be prepared, for example, by the hydrolysis of compounds of the general formula:

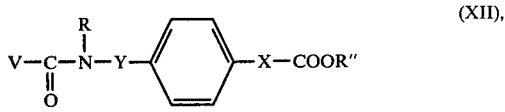

wherein Y, R and X have the same meanings as aboved and R" is a hydrogen atom or a lower alkyl radical, preferably a methyl or ethyl radical, and V is an aryl, lower alkyl or alkoxy radical, in an acidic or alkaline medium.

The compounds of general formula (XII) in which V is a lower alkyl or alkoxy radical are also new and, in the same way as compounds of general formula (I), possess hypoglycaomic and/or hypolipidaemic properties.

The oxidizable group B of compounds of general formula (III) is preferably a hydroxymethyl, aminomethyl or formyl radical or a functional derivative thereof, which can be easily oxidized to a carboxyl group with conventional oxidation agents, for example, permanganates or dichromates or, in the case of the formyl group, also with atmospheric oxygen.

The compounds of general formula (III), used as starting materials in process (b), are also new and, as precursors of compounds of general formula (i), also possess hypoglycaemic and/or hypolipidaemic properties.

They can be prepared in known manner, especially in a manner analogous to that according to method (a), but, instead of the acid of general formula (II), there is used a corresponding compound with an oxidizable group B. Of course, on the other hand, compounds of general formula (I) or the acid derivatives thereof, for example, the esters, acid halides and acid amides, can be converted into compounds of general formula (III) by reduction.

The ketocarboxylic acid derivatives of general formula (IV) used as starting materials in method (c) can, when Z ' is a valency bond, be prepared by the reaction of a compound of the general formula:

wherein A, R and Y have the same meanings as above, with an acid ester halide of the general formula:

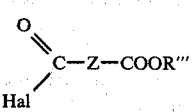

wherein Hal in a chlorine or bromine atom, Z is a straight or branched, saturated or unsaturated divalent aliphatic hydrocarbon radical containing up to 7 carbon atoms and R''' is a lower alkyl radical, preferably a methyl or ethyl radical, under the conditions of a Friedel-Crafts reaction. The esters so obtained can be subsequently saponified to give the corresponding acids. Instead of an acid ester halide, there can possibly also be used an acid anhydride of the general formula:

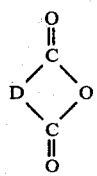

wherein D is a straight or branched, saturated or unsaturated divalent aliphatic hydrocarbon radical containing 2 to 7 carbon atoms.

When Z' is other than a valency bond, the ketocarboxylic acid derivatives of general formula (IV) used as starting materials in method (c) can be prepared by known methods, for example by a Claisen ester condensation.

The compounds of general formula (IV) used as starting materials in process (c) are also new and also possess hypoglycaemic and/or hypolipidaemic properties.

The reduction of the compounds of general formula (IV), wherein G is a keto group, can be carried out, for example, with the use of zinc/hydrochloric acid in the manner of a Clemmensen reduction or with hydrazine/alkali in the manner of a Wolff-Kishner reduction. However, the reduction is preferably carried out catalytically in the presence of a noble metal, for example, palladium or platinum. In this case, the solvent used is preferably a lower alcohol. However, it is also possible to work in glacial acetic acid to which has been added a trace of sulphuric or perchloric acid or molar amounts of hydrochloric acid. The reaction temperature is preferably 20° to 60° C. and the pressure used is preferably from 1 to 10 ats. of hydrogen.

The compounds of general formula (IV) in which G is a —CH(OH)— group can be prepared, for example, by reduction of the corresponding keto derivatives. The reduction can be carried out catalytically in the presence of noble metals, for example palladium or platinum. Complex metal hydrides can also be used as reduction agents. Sodium borohydride is preferably used. In this case, the reaction can be carried out in an alcohol, especially in methanol, or also in an aqueous alkaline medium. The halogen derivatives can be prepared from the hydroxy compounds by commonly known methods. The reduction to compounds of general formula (I) can be carried out under the above-described conditions (G is a keto group).

The reaction according to method (d) is carried out under the well-known conditions of the Perkin reaction or of the Knoevenagel reaction. The acid derivatives prepared according to Cope's variation are subsequently saponified to the acid, with decarboxylation. The lower alkyl radical P is an alkyl radical containing up to 5 carbon atoms and especially a methyl or ethyl radical. The cinnamic acid derivatives thus prepared can then be hydrogenated to the saturated compounds, for example catalytically with the use of palladium or platinum.

The compounds of general formula (VII) used in method (e) can be prepared by the reduction of the corresponding oxo derivatives. As reducing agents, there can be used complex metal hydrides, preferably sodium borohydride, lithium borohydride or hydrogen in the presence of palladium or platinum. The reaction with compounds of general formula (VIII) is carried out in a strongly acidic medium, for example, in 90% sulphuric acid. Hal is to be understood to be, in particular, chlorine.

The ketones of general formula (IX) used in method (f) can easily be prepared by a Friedel-Crafts acylation. The thiomorpholides obtained by the Villgerodt-Kindler synthesis are preferably saponified in an alkaline medium.

The reaction according to method (g) is carried out in known manner by the alkylation of β-dicarbonyl compounds. The lower alkyl radicals $R_2$ are to be understood to be alkyl radicals containing up to 5 carbon atoms and preferably methyl or ethyl radicals.

The esters obtained as intermediates in the above-described processes can be isolated or possibly saponified directly to give the corresponding carboxylic acids. On the other hand, carboxylic acids obtained can, again according to known methods, be reacted to give the desired esters.

Saponification of the esters, nitriles, amides and the like is preferably carried out in an alkaline medium.

Esterification of the carboxyl group can, in principle, be carried out with any alcohol. The lower monohydroxy alcohols are preferred, such as methanol, ethanol or propanol, as well as polyhydroxy alcohols, for example, glycol, or alcohols with other functional groups, for example ethanolamine or glycol monoethers.

The amides of general formula (I) according to the present invention can be prepared in known manner from the carboxylic acids or from reactive derivatives thereof by reaction with ammonia or amines. The amines used can be, for example, alkylamines, dialkylamines and the like; however, it is preferable to use amino acids, for example, p-aminobenzoic acid, anthranilic acid, phenylalanine and β-alanine.

As physiologically compatible salts, the alkali metal, alkaline earth metal and ammonium salts are especially preferred, as well as salts with blood sugar-reducing active compounds, preferably biguanides. The preparation of these salts is carried out in known manner, for example by reaction with the appropriate free bases or carbonates.

The blood sugar-reducing and/or anti-hyperlipidaemic compositions according to the present invention can be all conventional oral and parenteral forms of administration, for example, tablets, capsules, dragees, syrups, solutions, suspensions, drops, suppositories and the like. For this purpose, at least one active material is mixed with a solid or liquid pharmaceutical carrier or diluent and subsequently brought into the desired form. Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain flavoring and/or sweetening materials. As injection medium, it is preferred to use water which contains conventional additives for injection solutions, such as stabilizing agents, solubilizing agents and/or buffers. Additives of this type include, for example, acetate and tartrate buffers, ethanol, complex-forming agents (such as ethylenediamine-tetraacetic acid and the non-toxic salts thereof) and high molecular weight polymers (such as liquid polyethylene oxide) for viscosity regulation.

The following examples are given for the purpose of illustrating the present invention:

EXAMPLE 1.

β-{4-[2-(6-Chlorochromane-2-carboxamido)-ethyl]-phenyl}-propionic acid.

A solution of 2.8 g. 6-chlorochromane-2-carboxylic acid chloride in 20 ml. methylene chloride is added at 0° C. to a solution of 3.1 g. ethyl β-[4-(2-aminoethyl)-phenyl]-propionate hydrochloride in 24 ml. 1N aqueous sodium hydroxide solution. The reaction mixture is stirred for 3 hours at 20° C., acidified with 2N hydrochloric acid and the separated organic phase is shaken out with an aqueous solution of sodium bicarbonate. The methylene chloride solution is evaporated and the residue is heated on a waterbath for 1 hour with 20 ml. ethanol/20 ml. 1N aqueous sodium hydroxide solution. After evaporation of the ethanol, the residue is extracted with diethyl ether and the aqueous phase acidified. The precipitate obtained is recrystallized from isopropanol to give 2.4 g. (about 52% of theory) β-{4-[2-(6-chlorochromane-2-carboxamido)-ethyl]-phenyl}-propionic acid; m.p. 128°–130° C.

The ethyl β-[4-(2-aminoethyl)-phenyl]-propionate hydrochloride used as starting material can be prepared as follows:

Variant I 4-(2-Acetamidoethyl)-benzoic acid is reduced, via a mixed anhydride, with sodium borohydride to give 4-(2-acetamidoethyl)-benzyl alcohol (m.p. 72°–73° C.) and then oxidized with activated manganese dioxide to give 4-(2-acetamidoethyl)-benzaldehyde (m.p. 81°–83° C.). Subsequent reaction with malonic acid gives 4-(2-acetamidoethyl)-cinnamic acid (m.p. 206°–208° C.), which is hydrogenated to give β-[4-(2-acetamidoethyl)-phenyl]-propionic acid (m.p. 132°–133° C.). This is then subjected to acidic saponification and reacted directly with ethanol to give ethyl β-[4-(2-aminoethyl)-phenyl]-propionate hydrochloride (m.p. 165°–167° C.).

Variant II

N-Acetyl-phenethylamine is reacted with ethyl malonate chloride to give ethyl β-oxo-β-[4-(2-acetamidoethyl)-phenyl]-propionate (m.p. 89°–92° C.), which is reduced to ethyl β-[4-(2-acetamidoethyl)-phenyl]-propionate (m.p. 96°–98° C.) and this then subjected to alkaline saponification to give β-[4-(2-aminoethyl)-phenyl]-propionic acid (m.p. 270°–272° C.) followed by esterification to give the desired ethyl ester hydrochloride.

The following compounds are obtained in an analogous manner:

1. By the reaction of ethyl β-[4-(2-aminoethyl)-phenyl]-propionate hydrochloride with the appropriate carboxylic acid chlorides:

(a) β-{4-[2-(4-chlorobenzamido)-ethyl]-phenyl}-propionic acid; m.p. 171°–173° C., after reprecipitation;

(b) β-{4-[2-(3-trifluoromethylbenzamido)-ethyl]-phenyl}-propionic acid; m.p. 113°–115° C., after recrystallization from toluene;

(c) β-{4-[2-(2-butoxybenzamido)-ethyl]-phenyl}-propionic acid; m.p. 86°–88° C., after recrystallization from ethyl acetate;

(d) β-{4-[2-(2-methylthiobenzamido)-ethyl]-phenyl}-propionic acid; m.p. 135°–136° C., after recrystallization from methanol;

(e) β-{4-[2-methoxy-5-methylbenzamido)-ethyl]-phenyl}-propionic acid; m.p. 97°–99° C., after recrystallization from toluene;

(f) β-{4-[2-(5-chloro-2-methoxybenzamido)-ethyl]-phenyl}-propionic acid; m.p. 118°–120° C., after recrystallization from ethyl acetate;

(g) β-{4-[2-(2-aryloxy-5-chlorobenzamido)-ethyl]-phenyl}-propionic acid; m.p. 91°–93° C., after recrystallization from ethyl acetate;

(h) β-{4-[2-(2-allyloxy-5-chlorobenzamido)-ethyl]-phenyl}-propionic acid; m.p. 118°–120° C., after recrystallization from toluene;

(i) β-{4-[2-(5-fluoro-2-methoxybenzamido)-ethyl]-phenyl}-propionic acid; m.p. 126°–128° C., after recrystallization from isopropanol;

(j) β-{4-[2-(5-chloro-2-phenoxybenzamido)-ethyl]-phenyl}-propionic acid; m.p. 102°–105° C., after recrystallization from isopropanol; the compound contains 1.5 moles water of crystallization;

(k) β-{4-[2-(2,5-dichlorobenzamido)-ethyl]-phenyl}-propionic acid; m.p. 189°–191° C., after recrystallization from methanol;

(l) β-{4-[2-(2,5-dimethoxybenzamido)-ethyl]-phenyl}-propionic acid; m.p. 77°–79° C., after recrystallization from isopropanol/toluene;

(m) β-{4-[2-(3,5-dichloro-2-methoxybenzamido)-ethyl]-phenyl}-propionic acid; m.p. 108°–110° C., after recrystallization from isopropanol/water;

(n) β-{4-[2-(2-phenylpropionamido)-ethyl]-phenyl}-propionic acid; m.p. 124°–126° C., after recrystallization from isopropanol;

(o) β-{4-[2-(5-chloro-2-methoxycinnamoyl-amino)-ethyl]-phenyl}-propionic acid; m.p. 144°–145° C., after recrystallization from isopropanol/water;

(p) β-{4-[2-(5-chloro-3-methoxythenoyl-(2)-amino)-ethyl]-phenyl}-propionic acid; m.p. 123°–124° C., after recrystallization from isopropanol;

(q) β-[4-(2-nicotinoylaminoethyl)-phenyl]-propionic acid; m.p. 180° C., after recrystallization from isopropanol/water;

(r) β-{4-[2-(5-chloro-2-methyl-2,3-dihydrobenzo[b]-furoyl-(7)-amino)-ethyl]-phenyl}-propionic acid; m.p. 145° C., after recrystallization from isopropanol;

(s) β-{4-[2-(4-methylindole-2-carboxamido)-ethyl]-phenyl}-propionic acid; m.p. 168°–170° C., after recrystallization from methanol.

2. (a) By the reaction of ethyl γ-[4-(2-aminoethyl)-phenyl]-butyrate hydrochloride with 5-chloro-2-methoxybenzoyl chloride:
   γ-{4-[2-(5-chloro-2-methoxybenzamido)-ethyl]-phenyl}-butyric acid; m.p. 107°–109° C., after recrystallization from benzene;

(b) By the reaction of ethyl γ-[4-2-aminomethyl)-phenyl]-butyrate hydrochloride with 5-chloro-2-methoxybenzoyl chloride:

sodium γ-{4-[(5-chloro-2-methoxybenzamido)-methyl]-phenyl}-butyrate; m.p. 127°–130° C.

The acid was isolated in the form of its sodium salt. The ethyl γ-[(4-aminomethyl)-phenyl]-butyrate hydrochloride used for this purpose is prepared in the following manner:

Ethyl γ-phenylbutyrate is chloromethylated to give ethyl γ-(4-chloromethylphenyl)-butyrate (b.p. 123°–125° C./0.01 mm.Hg.) and from this, by means of the Gabriel synthesis, there is prepared ethyl γ-[(4-aminomethyl)-phenyl]-butyrate hydrochloride; m.p. 152°–155° C.

3. By the reaction of ethyl δ-[4-(2-aminoethyl)-phenyl]-valerate hydrochloride (m.p. 148°–152° C.) with 5-chloro-2-methoxybenzoyl chloride:
δ-{4-[2-(5-chloro-2-methoxybenzamido)-ethyl]-phenyl}-valeric acid; m.p. 95°–97° C., after recrystallization from benzene/isopropanol.

4. By the reaction of ethyl α-methyl-β-[4-(2-aminoethyl)-phenyl]-propionate hydrochloride (oil) with 5-chloro-2-methoxybenzoyl chloride:
β-methyl-β-{4-[2-(5-chloro-2-methoxybenzamido)-ethyl]-phenyl}-propionic acid; m.p. 109°–113° C., after recrystallization from dilute acetic acid.

The ester hydrochloride used as starting material is prepared in the following manner: α-methyl-4-(2-acetamidoethyl)-cinnamic acid (m.p. 145°–149° C.) is hydrogenated to give α-methyl-β-[4-(2-acetamidoethyl)-phenyl]-propionic acid (oil), then saponified to give the hydrochloride of α-methyl-β-[4-(2-aminoethyl)-phenyl]-propionic acid, followed by esterification to give the desired ethyl ester hydrochloride.

5. By the reaction of ethyl β-(4-aminophenyl)-propionate hydrochloride with 5-chloro-2-methoxybenzoyl chloride. there is obtained β-[4-(5-chloro-2-methoxybenzamido)-phenyl]-propionic acid; m.p. 188°–190° C., after recrystallization from ethanol.

6. By the reaction of ethyl β-[4-(2-aminopropyl)-phenyl]-propionate hydrochloride (m.p. 115°–117° C.) with 5-chloro-2-methoxybenzoyl chloride, there is obtained β-{4-[2-(5-chloro-2-methoxybenzamido)-propyl]-phenyl}-propionic acid; m.p. 125°–126° C., after recrystallization from isopropanol/water.

The ester hydrochloride used as starting material is prepared in the following manner: N-acetyl-4-acetylamphetamino (m.p. 99°–100° C.) is oxidized to 4-(2-acetamidopropyl)-benzoic acid (m.p. 207°–208° C.), this is reduced to give 4-(2-acetamidopropyl)-benzyl alcohol (oil) which is then oxidized to 4-(2-acetamidopropyl)-benzaldehyde (m.p. 84°–86° C.) and this is condensed with malonic acid to give 4-(2-acetamidopropyl)-cinnamic acid (m.p. 207°–208° C.) which is hydrogenated to give β-[4-(2-acetamidopropyl)-phenyl]-propionic acid (m.p. 93°–96° C.). Subsequent acid hydrolysis gives the hydrochloride of β-[4-(2-aminopropyl)-phenyl]-propionic acid which is esterified to give the above-mentioned ethyl ester hydrochloride.

7. By the reaction of ethyl α-methyl-4-(2-aminoethyl)-cinnamate hydrochloride (m.p. 270° C.) with 5-chloro-2-methoxybenzoyl chloride, there is obtained α-methyl-4-[2-(5-chloro-2-methoxybenzamido)-ethyl]-cinnamic acid; m.p. 188°–191° C., after recrystallization from ethanol.

8. By the reaction of ethyl β-{4-[2-(N-methylamino)-ethyl]-phenyl}-propionate hydrochloride (m.p. 162°–164° C.) with 5-chloro-2-methoxybenzoyl chloride, there is obtained β-{4-[2-(N-methyl-5-chloro-2-methoxybenzamido)-ethyl]-phenyl}-propionic acid; m.p. 152°–153° C., after recrystallization from toluene.

The ester hydrochloride used as starting material is prepared in the following manner: 4-[2-(N-methylacetamido)-ethyl]-acetophenone is reacted to give 4-[2-(N-methylacetamido)-ethyl]-benzoic acid (m.p. 149°–151° C.), then reduced to 4-[2-(N-methylacetamido)-ethyl]-benzyl alcohol (oil) and subsequently oxidized to 4-[2-(N-methylacetamido)-ethyl]-benzaldehyde (m.p. 54°–59° C.). After condensation thereof with malonic acid, there is obtained 4-[2-(N-methylacetamido)-ethyl]-cinnamic acid (m.p. 157°–158° C.) which is hydrogenated to give β-{4-[2-(N-methylacetamido)-ethyl]-phenyl}-propionic acid (m.p. 133°–134° C.). After hydrolysis, there is obtained the hydrochloride of β-{4-[2-(N-methylamino)-ethyl]-phenyl}-propionic acid (m.p. 211°–212° C.) and from this, by esterification, the above-mentioned ethyl ester hydrochloride.

9. By reaction of ethyl β-[4-(aminomethyl)-phenyl]-propionate hydrochloride (m.p. 192°–193° C.) with 5-chloro-2-methoxybenzoyl chloride, there is obtained β-[4-(5-chloro-2-methoxybenzamidomethyl)-phenyl]-propionic acid; m.p. 152°–153° C., after recrystallization from isopropanol.

The ester hydrochloride used as starting material is prepared in the following manner: 4-cyanocinnamic acid is reduced to give β-[4-(aminomethyl)-phenyl]-propionic acid hydrochloride (m.p. 210°–212° C.) and this then esterified to give the above-mentioned ethyl ester hydrochloride.

10. By the reaction of ethyl γ-[4-(2-aminoethyl)-phenyl]-but-2-ene-carboxylate hydrochloride with 5-chloro-2-methoxybenzoyl chloride, there is obtained γ-{4-[2-(5-chloro-2-methoxybenzamido)-ethyl]-phenyl}-but-2-ene-carboxylic acid; m.p. 180°–183° C., after reprecipitation.

11. By the reaction of ethyl α,α-dimethyl-β-[4-(2-aminoethyl)-phenyl]-propionate hydrochloride with 5-chloro-2-methoxybenzoyl chloride, there is obtained α,α-dimethyl-β-{4-[2-(5-chloro-2-methoxybenzamido)-ethyl]-phenyl}-propionic acid; m.p. 138°–141° C., after recrystallization from ethyl acetate.

The ethyl α,α-dimethyl-β-[4-(2-aminoethyl)-phenyl]-propionate hydrochloride (m.p. 113°–117° C.) used as starting material is prepared in the following manner: N-acetylphenethylamine is reacted with dimethylmalonic acid methyl ester chloride according to Friedel-Crafts method to give methyl α,α-dimethyl-β-oxo-β-[4-(2-acetamidoethyl)-phenyl]-propionate (b.p. 215°–220° C./0.1 mm.Hg.), this then reduced, via methyl α,α-dimethyl-β-hydroxy-β-[4-(2-acetamidoethyl)-phenyl]-propionate (m.p. 120°–123° C.) to give methyl α,α-dimethyl-β-[4-(2-acetamidoethyl)-phenyl]-propionate (b.p. 180°–190° C./0.1 mm Hg.), saponified to give α,α-dimethyl-β-[4-(2-aminoethyl)-phenyl]-propionic acid hydrochloride (m.p. 230°–235° C.) and thereafter esterified to give the desired ethyl ester hydrochloride.

12. By the reaction of ethyl 6-[4-(2-aminoethyl)-phenyl]-hexane-carboxylate hydrochloride (m.p. 182°–185° C.) with 5-chloro-2-methoxybenzoyl chloride to give 6-{4-[2-(5-chloro-2-methoxybenzamido)-ethyl]-phenyl}-hexane-carboxylic acid; m.p. 36° C., after recrystallization from toluene.

The ester hydrochloride used as starting material is prepared as follows: N-acetylphenethylamine is reacted, according to Friedel-Crafts method, with adipic acid methyl ester chloride (b.p. 113°–116° C./17 mm Hg.) to give methyl 6-oxo-6-[4-(2-acetamidoethyl)-phenyl]-hexane-carboxylate (oil) and then reduced to methyl 6-[4-(2-acetamidoethyl)-phenyl]-hexane-carboxylate (oil). After alkaline hydrolysis (m.p. of the amino acid 200°–205° C.) and subsequent esterification with ethanol, there is obtained the above-mentioned ethyl ester hydrochloride.

13. By the reaction of ethyl 6-[4-(2-aminoethyl)-phenyl]-hexane-carboxylate hydrochloride with 4-chlorobenzoyl chloride, there is obtained 6-{4-[2-(4-chlorobenzamido)-ethyl]-phenyl}-hexane-carboxylic acid; m.p. 140°–143° C., after recrystallization from ethanol/diethyl ether.

14. By the reaction of ethyl 7-[4-(2-aminoethyl)-phenyl]-heptane-carboxylate hydrochloride (m.p. 137°–139° C.) with 5-chloro-2-methoxybenzoyl chloride, there is obtained 7-{4-[2-(5-chloro-2-methoxybenzamido)-ethyl]-phenyl}-heptane-carboxylic acid; m.p. 103°–106° C., after recrystallization from diethyl ether.

The ester hydrochloride used as starting material is prepared in the following manner: N-acetylphenethylamine is reacted, according to Friedel-Crafts method, with the acid chloride of pimelic acid monomethyl ester (b.p. 125°–128° C./17 mm Hg.) to give methyl 7-oxo-7-[4-(2-acetamidoethyl)-phenyl]-heptane-carboxylate (oil), then saponified to give the corresponding carboxylic acid (m.p. 97°–100° C.) and subsequently reduced to 7-[4-(2-acetamidoethyl)-phenyl]-heptane-carboxylic acid (m.p. 108°–110° C.). After alkaline hydrolysis and subsequent esterification with ethanol, there is obtained the above-mentioned ethyl ester hydrochloride.

15. By the reaction of ethyl 7-[4-(2-aminoethyl)-phenyl]-heptane-carboxylate hydrochloride with 4-chlorobenzoyl chloride, there is obtained 7-{4-[2-(4-chlorobenzamido)-ethyl]-phenyl}-heptane-carboxylic acid; m.p. 145°–148° C., after recrystallization from diethyl ether.

16. By the reaction of ethyl 9-[4-(2-aminoethyl)-phenyl]-nonane-carboxylate hydrochloride (m.p. 135°–138° C.) with 5-chloro-2-methoxybenzoyl chloride, there is obtained 9-{4-[2-(5-chloro-2-methoxybenzamido)-ethyl]-phenyl}-nonane-carboxylic acid; m.p. 97°–100° C., after recrystallization from ethyl acetate.

The ester hydrochloride used as starting material is prepared in the following manner: N-acetylphenethylamine is reacted, according to Friedel-Crafts method, with the said chloride of azelaic acid monomethyl ester (b.p. 148°–150° C./12 mm Hg.) to give methyl 9-oxo-9-[4-(2-acetamidoethyl)-phenyl]-nonane-carboxylate (oil), saponified to give the corresponding carboxylic acid (m.p. 106°–108° C.) and then reduced to 9-[4-(2-acetamidoethyl)-phenyl]-nonane-carboxylic acid (m.p. 115°–118° C.). After alkaline hydrolysis and subsequent esterification with ethanol, there is obtained the above-mentioned ethyl ester hydrochloride.

EXAMPLE 2

4-[2-(4-chlorobenzamido)-ethyl]-cinnamic acid 30 ml. acetone are added to a solution of 4.9 g. 4-(2-aminoethyl)-cinnamic acid hydrochloride (m.p. >300° C.) in 22 ml. 1N aqueous sodium hydroxide solution and then a solution of 3.75 g. 4-chlorobenzoyl chloride in 15 ml. acetone is added thereto dropwise, together with a further 22 ml. 1N aqueous sodium hydroxide solution. The reaction mixture is further stirred for 2 hours at 20° C., acidified and the precipitate obtained is filtered off with suction and then recrystallized from ethanol. There are obtained 4.32 g. (about 61% of theory) 4-[2-(4-chlorobenzamido)-ethyl]-cinnamic acid; m.p. 253°–255° C.

EXAMPLE 3

$\beta$-[4-(2-Phenylthioacetamidoethyl)-phenyl]-propionic acid

A solution of 2.9 g. phenylthioacetyl chloride in 40 ml. anhydrous methylene chloride is added dropwise at 0° C. to a solution of 3.5 g. ethyl $\beta$-[4-(2-aminoethyl)-phenyl]-propionate and 1.6 g. triethylamine in 30 ml. anhydrous methylene chloride. After 30 minutes at 0° C. and 2 hours at 20° C., the reaction mixture is extracted with water and the organic phase is dried and evaporated. The residue (6.0 g.) is boiled with a solution of 1.3 g. sodium hydroxide in 50 ml. ethanol for 1 hour on a waterbath. The precipitated sodium salt is filtered off with suction, dissolved in water and the acid precipitated out by the addition of hydrochloric acid. The crude product obtained is recrystallized from isopropanol. There are thus obtained 2.3 g. (67% of theory) $\beta$-[4-(2-phenylthioacetamidoethyl)-phenyl]-propionic acid; m.p. 119°–122° C.

The following compounds are obtained in an analogous manner by the reaction of ethyl $\beta$-[4-(2-aminoethyl)-phenyl]-propionate with the appropriate acid chlorides:

(a) $\beta$-[4-(2-phenoxyacetamidoethyl)-phenyl]-propionic acid; m.p. 140°–141° C., after recrystallization from isopropanol;

(b) $\beta$-{4-[2-(6-chloroquinolino-8-carboxamido)-ethyl]-phenyl{-propionic acid; m.p. 210°–212° C., after reprecipitation.

EXAMPLE 4

$\beta$-{4-[2-(5-Bromo-2-methoxybenzamido)-ethyl]-phenyl}-propionic acid

A solution of 2.0 g. sodium bichromate and 1.5 ml. sulphuric acid in 20 ml. water is added to 7.84 g. 3-{4-[2-(5-bromo-2-methoxybenzamido)-ethyl]-phenyl}-propanol (m.p. 48°–50° C.) in 100 ml. methylene chloride. The reaction mixture is stirred for 6 hours at ambient temperature and the phases are separated. The organic layer is neutralized and, after drying, is evaporated. The residue is recrystallized from isopropanol to give 5.44 g. (67% of theory) $\beta$-{4-[2-(5-bromo-2-methoxybenzamido)-ethyl]-phenyl}-propionic acid; m.p. 120°–121° C.

EXAMPLE 5

$\gamma$-{4-[2-(4-Methylindole-2-carboxamido)-ethyl]-phenyl}-butyric acid 7.56 g. $\gamma$-oxo-$\gamma$-{4-[2-(4-methylindole-2-carboxamido)-ethyl]-phenyl}-butyric acid (m.p. 210°–212° C.) are hydrogenated on 50 ml. glacial acetic acid, with the addition of 0.5 g. palladium/charcoal and 0.5 ml. perchloric acid, at 1 at. pressure of hydrogen and at a temperature of 40° C. When the take up of hydrogen is finished, the reaction mixture is filtered, the solution is concentrated to one half of its volume and, while cooling, mixed with water. The solution is extracted several times with diethyl ether, the organic phase is evaporated and the residue obtained is recrystallized from toluene; there are obtained 3.42 g. (about 47% of theory) γ-{4-[2-(4-methylindole-2-carboxamido)-ethyl]-phenyl}-butyric acid; m.p. 132°-134° C.

EXAMPLE 6

4-[2-(5-Chloro-2methoxybenzamido)-ethyl]-cinnamic acid 31.75 g. 4-[2-(5-chloro-2-methoxybenzamido)-ethyl]-benzaldehyde (m.p. 115°-116° C.) and 1 ml. piperidine are added to 11.5 g. malonic acid in 100 ml. anhydrous pyridine. The reaction mixture is heated on a waterbath until the evolution of carbon dioxide is finished. After cooling, the reaction mixture is poured on to ice/concentrated hydrochloric acid and the precipitate formed is filtered off with suction, whereafter it is recrystallized from ethanol. There are obained 23.4 g. (about 65% of theory) 4-[2-(5-chloro-2-methoxybenzamido)-ethyl]-cinnamic acid; m.p. 197°-198° C.

EXAMPLE 7

4-[2-(5-Chloro-2-methoxybenzamido)-ethyl]-α-methyl-cinnamic acid 3.175 g. 4-[2-(5-chloro-2-methoxybenzamido)-ethyl]-benzaldehyde (m.p. 115°-116° C.), 1.3 g. propionic anhydride and 0.96 g. sodium propionate are allowed to react together for 30 hours at 130°-135° C. The reaction mixture is then mixed with 2N aqueous sodium hydroxide solution and extracted several times with methylene chloride and the aqueous phase is treated with active charcoal and then acidified. The precipitate obtained in recrystallized from ethanol. There are obtained 1.61 g. (about 45% of theory) 4-[2-(5-chloro-2-methoxybenzamido)-ethyl]-α-methylcinnamic acid; m.p. 188-191° C.

EXAMPLE 8

3-{4-[2-(5-Chloro-2-methoxybenzamido)-ethyl]-phenyl}-butyric acid

A mixture of 16.1 g. 1-{4-[2-(5-chloro-2-methoxybenzamido)-ethyl]-phenyl}-ethanol (oily product prepared by the reduction of 4-[2-(5-chloro-2-methoxybenzamido)-ethyl]-acetophenone (m.p. 99°-100° C.)) and 14.1 g. 1,1-dichloroethylene is added dropwise, within the course of 2 hours at 5° C. to 9.7 ml. 90% sulphuric acid. The reaction mixture is then poured on to ice, extracted with diethyl ether and the organic phase is extracted with 2 N aqueous sodium hydroxide solution and the aqueous phase acidified with concentrated hydrochloric acid. The oily product obtained is dissolved in an aqueous solution of sodium carbonate and precipitated out again by the addition of hydrochloric acid and subsequently taken up in ethyl acetate. The filtered solution is evaporated and the residue brought to crystallization with diethyl ether and water. There are obtained 3.08 g. (about 17% of theory) 3-{4-[2-(5-chloro-2-methoxybenzamido)-ethyl]-phenyl}-butyric acid; m.p. 125°-127° C.

EXAMPLE 9

β-[4-(2-Benzamido ethyl)-phenyl]-propionic acid 2.8 g. 4-(2-benzamidoethyl)-propiophenone (m.p. 127°-128° C.) are heated, within the course of 1 hour, to 100° C. with 0.5 g. sulphur and 3.5 g. morpholine and then boiled under reflux for 3 hours. After cooling somewhat, the reaction mixture is mixed with ethanol, filtered and the filtrate is well cooled and filtered with suction. There are obtained 3.2 g. of the thiomorpholide of β-[4-(2-benzamidoethyl)-phenyl]-propionic acid; m.p. 165°-168° C.

2 g. of this thiomorpholide are heated under reflux with a solution of 0.6 g. potassium hydroxide in 10 ml. ethanol for 3 hours. After evaporation, the reaction mixture is diluted with water, treated with active charcoal, filtered and the filtrate acidified with concentrated hydrochloric acid. The product is filtered off with suction and then recrystallized from isopropanol. The β-[4-(2-benzamidoethyl)-phenyl]-propionic acid thus obtained has a melting point of 164°-165° C.

EXAMPLE 10

β-{4-[2-(5-Chloro-2-methoxybenzamido)-ethyl]-phenyl}-propionic acid 7.19 g. 4-[2-(5-chloro-2-methoxybenzamido)-ethyl]-cinnamic acid are hydrogenated in methanol, with the use of 1 g. palladium/barium sulphate, at ambient temperature. After taking up 1 mol hydrogen/mol of starting material, the hydrogenation is discontinued and the solution is filtered, evaporated and the residue recrystallised from isopropanol/water. These are obtained 6.14 g. (about 85% of theory) β-{4-[2-(5-chloro-2-methoxybenzamido)-ethyl]-phenyl}-propionic acid; m.p. 118°-120° C.

EXAMPLE 11

Salt of β-{4-[2-(5-chloro-2-methoxybenzamido)-ethyl]-phenyl }-propionic acid with phenethyl-biguanide 1.8 g. β-{4-[2-(5-chloro-2-methoxybenzamido)-ethyl]-phenyl }-propionic acid is dissolved in 30 ml. methanol, a solution of 0.12 g. sodium in 5 ml. methanol is added thereto and the reaction mixture is evaporated in a vacuum. The residue is dissolved in 30 ml. ethanol, mixed with 1.15 g. phenethyl-biguanide hydrochloride, boiled under reflux for 5 hours, suction filtered while hot and the filtrate evaporated. The residue is taken up in isopropanol and again precipitated out with diethyl ether. This procedure is repeated four times. The desired salt is then obtained in solid form with a melting point of 160°-162° C.

EXAMPLE 12

β-{4-[2-(5-Methoxyquinoline-8-carboxamido)-ethyl]-phenyl }-propionic acid hydrochloride 2.1 ml. phosphorus oxychloride and 8.9 ml. triethylamino are added at −15° C., while stirring, to 4.2 g. 5-methoxyquinoline-8-carboxylic acid and 5.35 g. ethyl β-[4-(2-aminoethyl)-phenyl]-propionate hydrochloride in methylene chloride. The reaction mixture is further stirred for 30 minutes at −15° C. and for 2 hours at +20° C., mixed with water and the organic phase shaken out with a dilute aqueous solution of sodium hydroxide and the methylene chloride phase neutralized and completely evaporated. The oily ethyl ester which is thus obtained is saponified for 1 hour at 80° C. with 50 ml. ethanol/50 ml. 2 N aqueous sodium hydroxide solution. The alcohol is stripped off on a rotavapor and the aqueous solution is extracted with methylene chloride and acidified. The precipitated crude product is recrystallized from isopropanol. There are obtained 2.9 g. (34% of theory) β-{4-[2-(5-methoxyquinoline-8-carboxamido)-ethyl]-phenyl}-propionic acid hydrochloride; m.p. 222°-225° C.

The following compounds are obtained in an analogous manner by the reaction of ethyl β-[4-(2-aminoethyl)-phenyl]-propionate hydrochloride with the appropriate carboxylic acids:

(a) β-{4-[2-(2-N,N-dimethylaminobenzamido)-ethyl]-phenyl}-propionic acid hydrochloride; m.p. 206°–208° C., after recrystallization from ethanol;

(b) β-{4-(2-[2-(5-methylpyrazine-2-carboxamido)-ethyl]-phenyl}-propionic acid; m.p. 164°–165° C., after recrystallization from isopropanol;

(c) β-{4-[2-(fluorenyl-(9)-acetamido)-ethyl]-phenyl}-propionic acid; m.p. 218°–219° C., after recrystallization from ethyl acetate;

(d) β-{4-[2-(6-bromoquinoline-S-carboxamido)-ethyl]-phenyl}-propionic acid; m.p. 212°–214° C., after recrystallization from ethanol/ethylene chloride;

(e) β-{4-[2-(2-methylquinoline-8-carboxamido)-ethyl]-phenyl}-propionic acid; m.p. 140°–141° C., after recrystallization from isopropanol;

(f) β-{4-[2-quinoline-8-carboxamido)-ethyl]-phenyl}-propionic acid hydrochloride; m.p. 204°–206° C., after recrystallization from isopropanol; the compound contains 1 mole water of crystallization;

(g) β-{4-[2-(5-bromo-2-methoxynicotinoylamino)-ethyl]-phenyl}-propionic acid; m.p. 124°–125° C., after recrystallization from isopropanol;

(h) β-{4-[2-(5-chloro-2-methylbenzoxazole-7-carboxamido)-ethyl]-phenyl}-propionic acid;

(i) β-{4-[2-(indole-7-carboxamido)-ethyl]-phenyl}-propionic acid; m.p. 107°–109° C., after recrystallization from toluene;

(j) β-{4-[2-(3,5-di-tert.-butyl-4-hydroxybenzamido)-ethyl]-phenyl}-propionic acid; m.p. 187°–191° C., after recrystallization from ethyl acetate;

(k) sodium β-{{4-{2-[3-(3,5-di-tert.-butyl-4-hydroxyphenyl)-propioniamido]-ethyl}-phenyl}}-propionate; m.p. 265°–268° C.

EXAMPLE 13

β-{4-[2-Methylpyrazole-3-carboxamido)-ethyl]-phenyl}-propionic acid.

1.27 ml. triethylamino and 0.85 ml. ethyl chloroformate are added at −10° C. to a solution of 1.12 g. 5-methylpyrazole-3-carboxylic acid in 25 ml. anhydrous tetrahydrofuran. After 15 minutes, a further 1.27 ml. triethylamine is added and then 2.57 g. ethyl β-[4-(2-aminoethyl)-phenyl]-propionate hydrochloride. The reaction mixture is stirred for 1 hour at +20° C., filtered with suction and the filtered is evaporated and the residue taken up in methylene chloride. After extraction with 2% hydrochloric acid, 2 N aqueous sodium hydroxide solution and neutralization, the solution is dried and evaporated. The crude ester thus obtained is heated under reflux for 1 hour with 0.6 g. sodium hydroxide in 30 ml. ethanol. After cooling, the precipitated sodium salt is filtered off with suction, dissolved in water and carefully acidified. The precipitate obtained is filtered off and recrystallized from 20% ethanol. There is obtained β-{4-[2-(5-methylpyrazole-5-carboxamido)-ethyl]-phenyl}-propionic acid in a yield of 22% of theory; m.p. 202°–205° C.

EXAMPLE 14

N-{{β-{4-[2-(5-Chloro-2-methoxybenzamido)-ethyl]-phenyl}-propionyl}}-p-aminobenzoic acid 2.2 g. triethylamine and 2.6 g. triethyl chloroformate are added at −10° C. to 7.22 g. β-{4-[2-(5-chloro-2-methoxybenzamido)-ethyl]-phenyl}-propionic acid in 100 ml. methylene chloride. After 30 minutes, a solution of 3.7 g. ethyl p-aminobenzoate in 40 ml. methylene chloride is added dropwise at this temperature, whereafter the reaction mixture is heated for 5 hours at 40° C., then extracted with 2 N hydrochloric acid, 2 N aqueous sodium hydroxide solution and water and the organic phase is dried and evaporated. The ethyl ester (m.p. 158°–162° C.) which thus precipitates out is heated for 30 minutes on a waterbath with 50 ml. ethanol/50 ml. 1 N aqueous sodium hydroxide solution, the ethanol is stripped off and the aqueous solution, after extraction with methylene chloride, is acidified. The precipitate obtained is filtered off with suction and recrystallized from isopropanol. There are obtained 3.5 g. (40% of theory) N-{{β-{4-[2-(5-chloro-2-methoxybenzamido)-ethyl]-phenyl}-propionyl}}-p-aminobenzoic acid; m.p. 216°–220° C.

In an analogous manner, there is obtained, by the reaction of β-{4-[2-(5-chloro-2-methoxybenzamido)-ethyl]-phenyl}-propionic acid:

with anthranilic acid ethyl ester:
N-{{β-{4-[2-(5-chloro-2-methoxybenzamido)-ethyl]-phenyl}-propionyl}}-anthranilic acid; m.p. 163°–165° C., after recrystallization from isopropanol;

with phenyl-alanine ethyl ester:
N-{{β-4-[2-(5-chloro-2-methoxybenzamido)-ethyl]-phenyl}-propionyl}}-phenylalanine; m.p. 152°–154° C., after recrystallization from isopropanol;

with β-alanine ethyl ester:
N-{{β-{4-[2-(5-chloro-2-methoxybenzamido)-ethyl]-phenyl}-propionyl}}-β-alanine; m.p. 127°–130° C. after recrystallization from isopropanol.

EXAMPLE 15

N-{4-[2-(5-Chloro-2-methoxybenzamido)-ethyl]-cinnamoyl}-p-aminobenzoic acid 4.5 g. 4-[2-(5-chloro-2-methoxybenzamido)-ethyl]-cinnamic acid and 2 g. ethyl p-aminobenzoate are dissolved in 100 ml. anhydrous tetrahydrofuran. At 20° C., there is first added 1 ml. phosphorus oxychloride and then 3 ml. triethylamine. After 4 hours, the reaction mixture is filtered off with suction, the filtrate is completely evaporated and the residue is mixed with 2 N aqueous sodium hydroxide solution and then extracted with chloroform. The organic phase is shaken out with 2 N hydrochloric acid, dried and evaporated. The ethyl ester (m.p. 118°–120° C.) which is thus obtained is saponified at ambient temperature with 30 ml. ethanol/10 ml. 2 N aqueous sodium hydroxide solution. After 24 hours, the precipitated sodium salt is filtered off with suction and thereafter well washed with ethanol and dissolved in a little water. After acidification, the desired compound precipitates out and is recrystallized from ethanol. There is obtained 1.1 g. (18% of theory) N-{4-[2-(5-chloro-2-methoxybenzamido)-ethyl]-cinnamoyl}-p-aminobenzoic acid; m.p. 258°–260° C. The product contains 1 mole water of crystallization.

EXAMPLE 16

In a manner analogous to that described in Example 1, by the reaction of ethyl β-[4-(2-aminoethyl)-phenyl]-propionate hydrochloride with the appropriate carboxylic acid chlorides, there are obtained the following compounds:

(a) β-{4-[2-(5-chloro-2-(β-methoxyethoxy)-benzamido)-ethyl]-phenyl}-propionic acid; m.p. 99°–101° C., after recrystallization from isopropanol;

(b) β-{4-[2-methoxy-naphthalene-1-carboxamido)-ethyl]-phenyl}-propionic acid; m.p. 124°–125° C., after recrystallization from isopropanol;

(c) β-{4-[2-(5-chloroindole-2-carboxamido)-ethyl]-phenyl}-propionic acid; m.p. 257°–258° C., after recrystallization from ethanol;

(d) β-{4-[2-(naphthalene-1-carboxamido)-ethyl]-phenyl}-propionic acid; m.p. 143°–144° C., after recrystallization from isopropanol;

(e) β-{4-[2-naphthalene-2-carboxamido)-ethyl]-phenyl}-propionic acid; m.p. 187°–188° C., after recrystallization from ethanol/water;

(f) β-{4-[2-(3-methoxynaphthalene-2-carboxamido)-ethyl]-phenyl}-propionic acid; m.p. 156°–157° C., after recrystallization from isopropanol;

(g) β-{4-[2-phenoxybenzamido)-ethyl]-phenyl}-propionic acid; m.p. 124°–125° C., after recrystallization from isopropanol;

(h) β-{4-[2-allyloxy-5-methylbenzamido)-ethyl]-phenyl}-propionic acid; m.p. 67°–69° C., after recrystallization from toluene;

(i) β-{4-[2-(3-chloro-5-methylbenzamido)-ethyl]-phenyl}-propionic acid; m.p. 158°–160° C., after recrystallization from isopropanol/water;

(j) β-{4-[2-(2-methoxy-5-trifluoromethylbenzamido)-ethyl]-phenyl}-propionic acid; m.p. 118°–121° C., after recrystallization from ethyl acetate;

(k) β-{4-[2-(4-bromo-2-methoxybenzamido)-ethyl]-phenyl}-propionic acid; m.p. 108°–111° C., after recrystallization from ethyl acetate;

(l) β-{4-[2-(5-chloro-2-methylbenzo[b]furoyl-(7)-amino)-ethyl]-phenyl}-propionic acid; m.p. 143°–145° C., after recrystallization from toluene;

(m) β-{4-[2-(quinoline-2-carboxamido)-ethyl]-phenyl}-propionic acid; m.p. 135°–137° C., after reprecipitation;

(n) β-{4-[2-(5-chloro-2-(4-methoxyphenoxy)-benzamido)-ethyl]-phenyl}-propionic acid; m.p. 199°–201° C., after recrystallization from ethanol;

(o) β-{4-[2-(5-methylisoxazole-3-carboxamido)-ethyl]-phenyl}-propionic acid; m.p. 164°–167° C., after recrystallization from ethanol;

(p) β-{4-[2-(2-ethoxy-5-methylbenzamido)-ethyl]-phenyl}-propionic acid; m.p. 82°–83° C., after recrystallization from xylene.

EXAMPLE 17

Methyl β-{4-[2-(5-chloro-2-methoxybenzamido)-ethyl]-phenyl}-propionate 3.62 g. β-{4-[2-(5-chloro-2-methoxybenzamido)-ethyl]-phenyl}-propionic acid (for the preparation thereof see Example 1f) are dissolved in 30 ml. methanol, gaseous hydrogen chloride is passed therein and the reaction mixture is boiled under refux for 10 hours. Thereafter, the reaction mixture is evaporated, the residue is mixed with 2N aqueous sodium hydroxide solution, extracted with ether and the ethereal phase dried and evaporated to dryness. There are obtained 2.2 g. (58% of theory) methyl β-{4-[2-(5-chloro-2-methoxybenzamido)-ethyl]-phenyl}-propionate; m.p. 58°–61° C.

EXAMPLE 18

In a manner analogous to that described in Example 2, there are obtained the following compounds by reaction with the indicated starting materials:

(a) β-(4-aminophenyl)-propionic acid with 2-ethoxy-5-chlorobenzoyl chloride;
β-[4-(2-ethoxy-5-chlorobenzamido)-phenyl]-propionic acid; m.p. 182° C., after recrystallization from ethanol;

(b) β-(4-aminophenyl)-propionic acid with 2-methoxy-5-methylbenzoyl chloride:
β-[4-(2-methoxy-5-methylbenzamido)-phenyl]-propionic acid; m.p. 164° C., after recrystallization from ethanol;

(c) 4-aminocinnamic acid with 5-chloro-2-methoxybenzoyl chloride:
4-(5-chloro-2-methoxybenzamido)-cinnamic acid; m.p. 285° C., after recrystallization from ethanol/dimethyl formamide;

(d) 4-aminocinnamic acid with 2-methoxy-5-methylbenzoyl chloride;
4-(2-methoxy-5-methylbenzamido)-cinnamic acid; m.p. 227° C., after recrystallization from ethanol/dimethyl formamide;

(e) 4-aminocinnamic acid with 2-ethoxy-5-chlorobenzoyl chloride:
4-(2-ethoxy-5-chlorobenzamido)-cinnamic acid; m.p. 278°–280° C., after recrystallization from ethanol/dimethyl formamide.

The hypoglycaemic activity of the test compounds was tested in known manner as follows:

The test compounds were administered (a) intraperitoneally, as a solution of the sodium salt, to fasting male Sprague-Dawley rats with a body weight of 200–220 g or (b) intravenously, as a solution of the sodium salt, to fasting rabbits of both sexes with an approximate body weight of 2 kg. In the following Table 1, there is given the threshold dosage, i.e. the lowest dosage of compound required to produce a significant reduction in the blood sugar level.

For purposes of comparison, $N_1$-(sulfanilyl)-$N_2$-(n-butyl)-urea (sold under trade name "Nadisan") was tested under the same conditions.

The results are set forth in Table 1 below.

Table 1

| Chemical Name of Active Material | Compound of Example No. | | Threshold Dosage [mg/kg] | |
|---|---|---|---|---|
| | | Rats, i.p. | Rabbits, i.v. | |
| $N_1$-(sulfanilyl)-$N_2$-(n-butyl)-urea | Comparison | 25 | 200 | |
| β-{4-[2-(6-chlorochromane-2-carboxamido)-ethyl]-phenyl}-propionic acid | 1 | 25 | 10 | |
| β-{4-[2-(3-trifluormethylbenzamido)-ethyl]-phenyl}-propionic acid | 1/1 b | 50 | 25 | |
| β-{4-[2-(2-butoxybenzamido)-ethyl]-phenyl}-propionic acid | 1/1 c | 5 (short) | 10 | |
| β-{4-[2-(2-methoxy-5-methylbenzamido)-ethyl]-phenyl}-propionic acid | 1/1 e | 15 | 25 | |
| β-{4-[2-(5-chloro-2-methoxybenzamido)-ethyl]-phenyl}-propionic acid | 1/1 f  10 | 5–10 | 10 | |
| β-{4-[2-(2-amyloxy)-5-chlorobenzamido)-ethyl]-phenyl}-propionic acid | 1/1 g | 5 (short) | 5 (short) | |

Table 1-continued

| Chemical Name of Active Material | Compound of Example No. | Threshold Dosage [mg/kg] Rats, i.p. | Threshold Dosage [mg/kg] Rabbits, i.v. |
|---|---|---|---|
| β-{4-[2-(2-allyloxy-5-chlorobenzamido)-ethyl]-phenyl}-propionic acid | 1/1 h | 10 | 5 |
| β-{4-[2-(5-chloro-2-phenoxybenzamido)-ethyl]-phenyl}-propionic acid | 1/1 j | 10 | 10 |
| β-{4[2-(5-fluoro-2-methoxybenzamido)-ethyl]-phenyl}-propionic acid | 1/1 i | 25 | 25 |
| β-{4-[2-(2,5-dimethoxybenzamido)-ethyl]-phenyl}-propionic acid | 1/1 l | 25 (short) | 25 (short) |
| β-{4-[2-(3,5-dichloro-2-methoxybenzamido)-ethyl]-phenyl}propionic acid | 1/1 m | 10 | 25 |
| β-{4-[2-(2-phenylpropionamido)-ethyl]-phenyl}-propionic acid | 1/1 n | 75 | 50 |
| β-{4-[2-(5-chloro-3-methoxythenoyl-(2)-amino)-ethyl]-phenyl}-propionic acid | 1/1 p | 25 | 25 |
| β-{4-[2-(5-chloro-2-methyl-2,3-dihydrobenzo[b]-furoyl-(7)-amino)-ethyl]-phenyl}-propionic acid | 1/1 r | 5 (short) | 10 |
| γ-4-[2-(5-chloro-2-methoxybenzamido)-ethyl]-phenyl}-butyric acid | ½ a | 50 | 40 |
| δ-{4-[2-(5-chloro-2-methoxybenzamido)-ethyl]-phenyl}-valeric acid | ½10 | 15 | |
| α-methyl-β-{4-[2-(5-chloro-2-methoxybenzamido)-ethyl]-phenyl}-propionic acid | ¼ | 10 | 25 |
| β-{4-[2-(5-chloro-2-methoxybenzamido)-propyl]-phenyl}-propionic acid | 1/6 | 15 (short) | 15 (short) |
| α-methyl-4-[2-(5-chloro-2-methoxybenzamido)-ethyl]-cinnamic acid | 1/7  7 | 10 | 20 |
| α,α-dimethyl-β-{4-[2-(5-chloro-2-methoxybenzamino)-ethyl]-phenyl} propionic acid | 1/11 | 25 | 25 (short) |
| 6-{4-[2-(5-chloro-2-methoxybenzamido)-ethyl]-phenyl-hexane-carboxylic acid | 1/12 | 50 | 25 |
| 7-{4-[2-(5-chloro-2-methoxybenzamido-ethyl]-phenyl}-heptane-carboxylic acid | 1/14 | 10-25 | 10 |
| 9-{4-[2-(5-chloro-2-methoxybenzamido)-ethyl]-phenyl]-nonane-carboxylic acid | 1/16 | 35 | |
| β-{4-[2-(5-chloroquinoline-8-carboxamido)-ethyl]-phenyl}-propionic acid | 3 b | 10-25 | 25 |
| β-{4-[2-(5-bromo-2-methoxybenzamido)-ethyl]-phenyl}-propionic acid | 4 | 10 | 10 |
| 4-[2-(5-chloro-2-methoxybenzamido)-ethyl]-cinnamic acid | 6 | 15 | 15 |
| 3-{4-[2-(5-chloro-2-methoxybenzamido)-ethyl]phenyl}-butyric acid | 8 | > 50 | 100 |
| β-[4-(2-benzamidoethyl)-phenyl]-propionic acid | 9 | 50 | > 50 |
| β-{4-[2-(6-bromoquinoline-8-carboxamido)-ethyl]-phenyl}-propionic acid | 12 d | 10 | 25 (short) |
| β-{4-[2-(2-methylquinoline-8-carboxamido)-ethyl]-phenyl}-propionic acid | 12 e | 10-25 (short) | 10 |
| β{4-[2-(quinoline-8-carboxamido)-ethyl]-phenyl}-propionic acid hydrochloride | 12 f | 50 | 25 (short) |
| N-{{β-{4-[2-(5-chloro-2-methoxybenzamido)-ethyl]-phenyl}-propionyl}}-p-aminobenzoic acid | 14 | 25 | 25 |
| N-{{β-{4-[2-(5-chloro-2-methoxybenzamido)-ethyl]-phenyl}-propionyl}}-anthranilic acid | 14 a | 50 | > 50 p. o. |
| N-{{β-{4-[2-(5-chloro-2-methoxybenzamido)-ethyl]-phenyl}-propionyl}}-phenylalanine | 14 b | 25 | 50 |
| N-{{β-{4-[2-(5-chloro-2-methoxybenzamido)-ethyl]-phenyl}-propionyl}}-β-alanine | 14 c | 25 | 75 |
| β-{4-[2-(5-chloro-2-(β-methoxyethoxy)-benzamido)-ethyl]-phenyl}-propionic acid | 16 a | 25 | 25 |
| β-{4-[2-(3-methoxynaphthalene-2-carboxamido)-ethyl]-phenyl}-propionic acid | 16 f | 25 | 50 |
| β-{4-[2-(2-phenoxybenzamido)-ethyl]-phenyl}-propionic acid | 16 g | 35 (short) | 15 (short) |
| β-{4-[2-(2-allyloxy-5-methylbenzamido)-ethyl]-phenyl}-propionic acid | 16 h | 10 | 25 |
| β-{4-[2-(3-chloro-5-methylbenzamido)-ethyl]-phenyl}-propionic acid | 16 i | 50 | 50 |
| β-{4-[2-(2-methoxy-5-trifluormethylbenzamido)-ethyl]-phenyl}-propionic acid | 16 j | 10 | 5 (short) |
| β-{4-[2-(4-bromo-2-methoxybenzamido)-ethyl]-phenyl}-propionic acid | 16 k | 25 | 25 |
| β-{4-[2-(5-chloro-2-methylbenzo[b]furoyl-(7)-amino)-ethyl]-phenyl}-propionic acid | 16 l | 10 | 10-25 |
| β-{4-[2-(2-ethoxy-5-methylbenzamido)-ethyl]-phenyl}-propionic acid | 16 p | 10-25 | 25 |
| β-{4-[2-(fluorenyl-(9)-acetamido)-ethyl]-phenyl}-propionic acid | 12 c | 2.5 | 1 |

The ability of the instant compounds to lower the serum lipid level and the cholesterol level is demonstrated by the following illustrative experiments:

Male rats of a weight of about 200 g (10 animals per substance in each case) were given for 6 days a powdered fodder of the company Intermast GmbH, Bockum-Hövel (manufacturer: Plange, Soest), which contained admixed thereto the substances to be tested in the concentrations listed below.

On the seventh day, without interruption of the feeding of the substances, the animals were killed by neck blow and bled white. The triglycerides in the serum were then determined enzymatically according to Kreutz and Eggstein (Klin. Wschr. 40,363/1962; 44,262/1966) in the modification according to Schmidt et al. (Z. Klin. chem and klin. Biochem. 6, 156/1968) and cholesterol was determined colorimetrically according to Watson (Klin. chim. Acta 5, 637/1960).

The results are set forth in Table 2 below:

Table 2

| Chemical Name of Active Material | Compound of Example No. | Dose, mg/kg | Reduction in % Triglyceride | Reduction in % Cholesterol |
|---|---|---|---|---|
| β-{4-[2-(4-chlorobenzamido)-ethyl]-phenyl}-propionic acid | 1/1 a | 50 | 40 | 15 |
| β-{4-[2-(5-chloro-2-methoxybenzamido)-ethyl]-phenyl}-propionic acid | 1/1 f | 50 | 55 | 24 |
| γ-{4-[2-(5-chloro-2-methoxybenzamido)-ethyl]-phenyl}-butyric acid | 1/2 a | 50 | 14 | 1 |
| α-methyl-β-{4-[2-(5-chloro-2-methoxybenzamido)-ethyl]-phenyl}-propio- | | | | |

| Chemical Name of Active Material | Compound of Example No. | Dose, mg/kg | Reduction in % Tri-glyceride | Cholesterol |
|---|---|---|---|---|
| nic acid | 1/4 | 50 | 31 | 12 |
| 4-[2-(5-chloro-2-methoxybenzamido)-ethyl]-cinnamic acid | 6 | 50 | 16 | 8 |
| 3-{4-[2-(5-chloro-2-methoxybenzamido)-ethyl]-phenyl}-butyric acid | 8 | 50 | 48 | 18 |

The novel compounds may be administered by themselves or in conjunction with carriers which are pharmacologically acceptable, either active or inert. The dosage units are similar to those of the heretofore known anti-cholesterol agents, e.g., about 0,2 to 2 grams per day for an adult or about 3-30 mg/kg per day although higher or lower dosages can be used. Rather than a single dose it is preferable if the compounds are administered in the course of a day, i.e., about four applications of 100 mg. each at spaced time intervals or 8 of about 50 mg. each. A convenient form of administration is in a gelatine capsule.

The dosage of the novel compounds of the present invention for the treatment of diabetes depends in the main on the age, weight, and condition of the patient being treated. The preferable form of administration is via the oral route in connection with which dosage units containing 50-500 mg. of active compound in combination with a suitable pharmaceutical diluent is employed. One or two unit dosages are good from one to four times a day.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

The compounds (I) can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents (such as ethylene diaminetetraacetic acid), high molecular weight polymers (such as liquid polyethylene oxide) for viscosity regulation or polyoxyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

As noted hereinabove the material administered may be the acid or a salt, ester or amide thereof. It is believed that due to hydrolysis in the body the active material is in all these instances the same, viz. probably the acid.

It will be appreciated that the instant specification and examples are set forth by way of illustration and not limitation, and that various modifications and changes may be made without departing from the spirit and scope of the present invention.

What is claimed is:

1. A phenyl-alkane-carboxylic acid of the formula

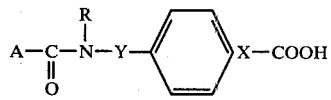

wherein
A is an aryl, aralkyl or arylvinyl radical optionally substituted by hydroxy, halogen, trifluoromethyl, alkyl, alkylthio, alkoxy, alkenyloxy, alkoxyalkoxy, alkyl-substituted amino, aryloxy or alkoxy-substituted aryloxy, or is an aryloxyalkyl or arylthioalkyl radical, or a thienyl or quinolyl radical optionally substituted by halogen, or alkyl or alkoxy containing up to 5 carbon atoms, any aryl moiety of A containing from 6 to 10 carbon atoms and any alkyl, alkoxy or alkenyloxy moiety of A containing 2 5 carbon atoms,
Y is an unbranched or branched lower alkylene radical containing up to 3 carbon atoms,
X is a straight or branched, saturated or unsaturated divalent aliphatic hydrocarbon radical containing 2 to 8 carbon atoms, there being at least 2 carbon atoms between the benzene ring and the carboxyl group, and
R is a hydrogen atom or a lower alkyl radical containing up to 5 carbon atoms,
or a physiologically compatible salt, ester or amide thereof.

2. A compound as claimed in claim 1, wherein A is phenyl, naphthyl or phenethyl optionally substituted by at least one of tert. butyl and hydroxyl, fluorenyl-(9)-methyl, styryl optionally substituted by at least one of fluorine, chlorine, bromine and alkoxy containing up to 5 carbon atoms, phenoxymethyl or phenylthiomethyl or thienyl or quinolyl, optionally substituted by at least one fluorine, chlorine, bromine and alkyl or alkoxy containing up to 5 carbon atoms.

3. A compound as claimed in claim 1, wherein such compound is
β-{4-[2-(5-chloro-2-methoxybenzamido)-ethyl]-phenyl}-propionic acid.

4. A compound as claimed in claim 1, wherein such compound is
δ-{4-[2-(5-chloro-2-methoxybenzamido)-ethyl]-phenyl}-valeric acid.

5. A compound as claimed in claim 1, wherein such compound is
α-methyl-β-{4-[2-(5-chloro-2-methoxybenzamido)-ethyl]-phenyl}-propionic acid.

6. A compound as claimed in claim 1, wherein such compound is
β-{4-[2-(fluorenyl-(9)-acetamido)-ethyl]-phenyl}-propionic acid.

7. A hypoglycaemic or hypolipidaemic composition comprising a hypoglycaemically or hypolipidaemically effective amount of a compound according to claim 1 in admixture with a physiologically compatible diluent.

8. A method for lowering the sugar or cholesterol or serum lipid level in a patient's blood which comprises administering to such patient a hypoglycaemically or hypolipidaemically effective amount of a compound according to claim 1.

9. The method as claimed in claim 8, wherein such compound is

β-{4-[2-(5-chloro-2-methoxybenzamido)-ethyl]-phenyl}-propionic acid,

δ-{4-[2-(5-chloro-2-methoxybenzamido)-ethyl]-phenyl}-valeric acid,

α-methyl-β-{4-[2-(5-chloro-2-methoxybenzamido)-ethyl]-phenyl}-propionic acid, or β-{4-[2-(fluorenyl-(9)-acetamido)-ethyl]-phenyl}-propionic acid or a physiologically compatible salt, ester or amide thereof.

* * * * *